(12) United States Patent
Miller

(10) Patent No.: US 9,125,698 B2
(45) Date of Patent: Sep. 8, 2015

(54) IMPLANTABLE TENSILE DEVICE FOR FIXATION OF SKELETAL PARTS AND METHOD OF USE THEREOF

(71) Applicant: Michael R. Miller, Churubusco, IN (US)

(72) Inventor: Michael R. Miller, Churubusco, IN (US)

( * ) Notice: Subject to any disclaimer, the term of this patent is extended or adjusted under 35 U.S.C. 154(b) by 273 days.

(21) Appl. No.: 13/775,406

(22) Filed: Feb. 25, 2013

(65) Prior Publication Data

US 2014/0243904 A1    Aug. 28, 2014

(51) Int. Cl.
*A61B 17/66* (2006.01)
*A61B 17/80* (2006.01)

(52) U.S. Cl.
CPC ......... *A61B 17/8019* (2013.01); *A61B 17/8085* (2013.01)

(58) Field of Classification Search
USPC ...................................... 606/57, 282, 105, 90
See application file for complete search history.

(56) References Cited

U.S. PATENT DOCUMENTS

| | | |
|---|---|---|
| 4,364,382 A | 12/1982 | Mennen |
| 5,201,737 A | 4/1993 | Leibinger et al. |
| 5,324,290 A | 6/1994 | Zdeblick et al. |
| 5,423,816 A | 6/1995 | Lin |
| 5,578,036 A | 11/1996 | Stone et al. |
| 5,743,913 A | 4/1998 | Wellisz |
| 6,001,099 A | 12/1999 | Huebner |
| 6,206,882 B1 | 3/2001 | Cohen |
| 6,348,052 B1 | 2/2002 | Sammarco |
| 6,761,719 B2 | 7/2004 | Justis et al. |
| 7,189,237 B2 | 3/2007 | Huebner |
| 7,842,037 B2 | 11/2010 | Schulze |
| 8,435,265 B2 * | 5/2013 | Konieczynski et al. ...... 606/246 |
| 2010/0076495 A1 | 3/2010 | Lindemann et al. |

\* cited by examiner

*Primary Examiner* — Sameh Boles
(74) *Attorney, Agent, or Firm* — George Pappas

(57) ABSTRACT

An implantable tensile device and method of use thereof for flexibly securing skeletal parts. The device includes a planar tensile portion between fixation ends adapted to be fastened to skeletal parts. The tensile portion includes flexure slots extending from its sides beyond a longitudinal central axis to a terminal bottom. The flexure slots are keyhole shaped. The fixation ends are fastened to the skeletal parts with screw fasteners. The device can be fastened to the skeletal parts after pre-tensioning with an extension tool such that the skeletal parts to which the fixation ends are fastened are biased toward one another. Without pre-tensioning, the skeletal parts are flexibly secured and further expansion thereof is resisted. Abutment elements on the fixation ends are engaged by the extension tool for pre-tensioning.

12 Claims, 10 Drawing Sheets

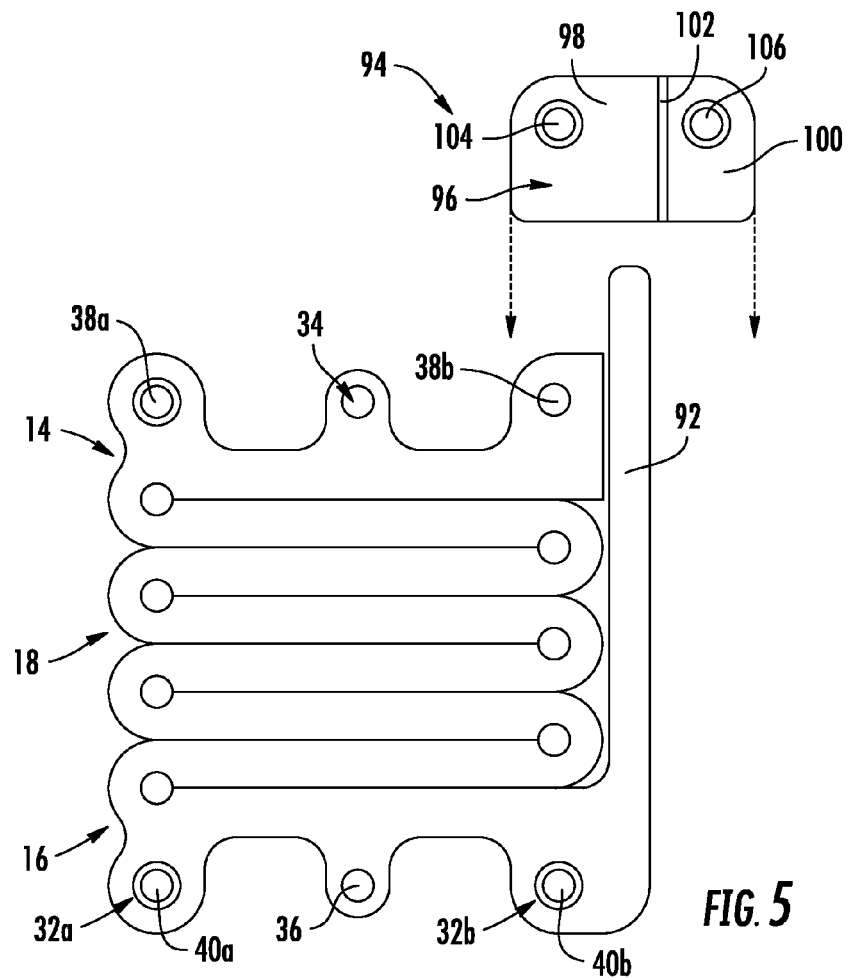
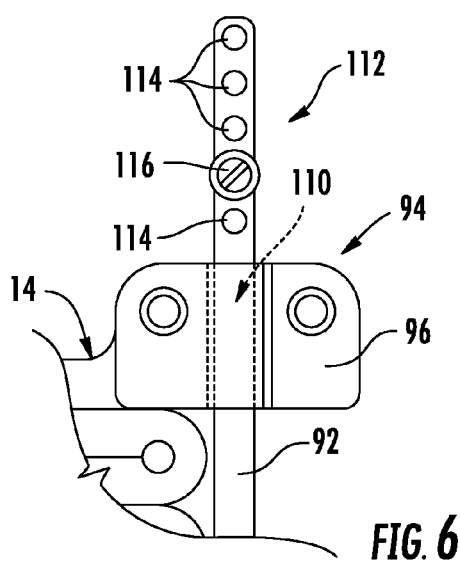
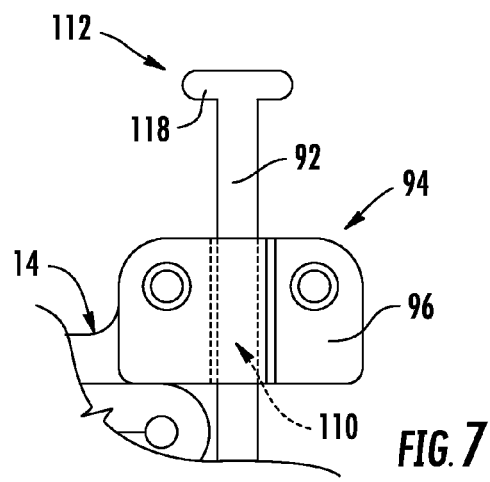

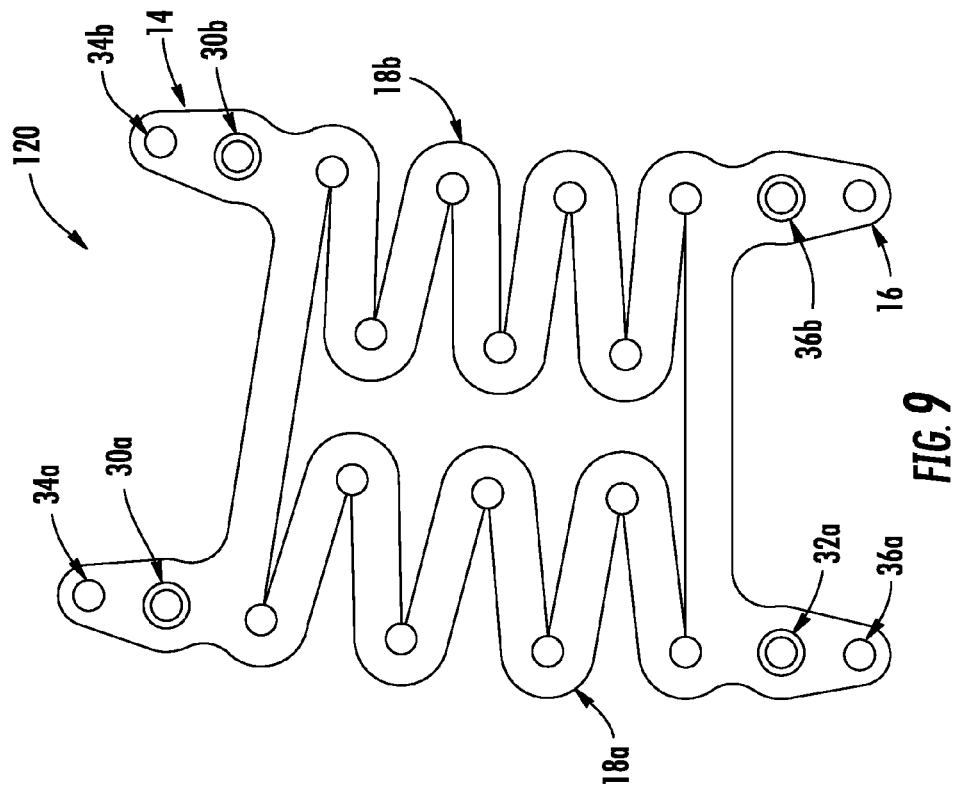
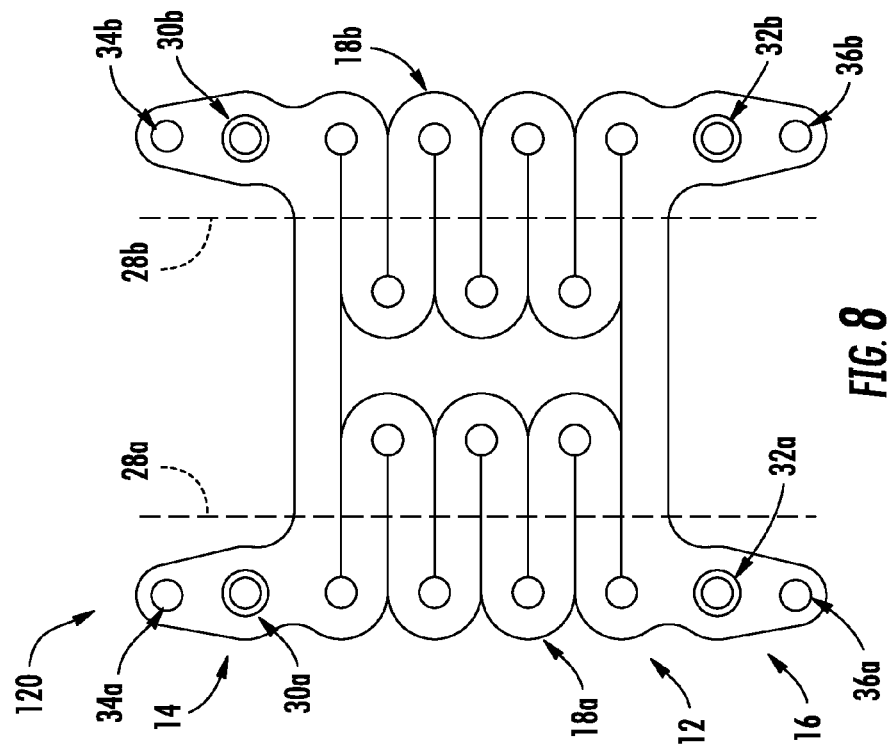

IMPLANTABLE TENSILE DEVICE FOR FIXATION OF SKELETAL PARTS AND METHOD OF USE THEREOF

BACKGROUND OF THE INVENTION

1. Field of the Invention

The present invention relates to the field of surgical implants for fixation of skeletal parts including bones and tendons. More particularly, the present invention relates to implantable tensile devices for fixation of skeletal parts and the use thereof whereby the skeletal parts to which the device is fastened are biased toward one another and/or expansion thereof is resisted.

2. Background

Devices for fixation of skeletal parts are today commonly used. These devices are made of biocompatible materials and are surgically implanted as needed, for example, in fastening fractured bones and torn tendons. Typically, they are fastened to the skeletal parts with treaded fasteners also made of biocompatible materials.

Some fixation devices are selectively flexibly deformable. For example, U.S. Pat. No. 6,206,882 discloses a flexibly deformable plate that includes flexure slots which enable a surgeon to more easily conform the plate to the surfaces of the skeletal parts. Fixation devices of this character are essentially rigid relative to the skeletal parts to which they are affixed and, therefore, do not provide any expansion that may be needed, for example, as a result of swelling.

Other fixation devices are flexibly elastic. For example, U.S. Pat. No. 6,761,719 discloses a spinal stabilization device made of shape memory material whereby, upon securement to vertebral bodies, the device will reform in response to the imposition of stress caused by displacement of the vertebral bodies and will recover to its initial configuration when the stress is removed.

Yet other flexible fixation devices are disclosed in U.S. Pat. No. 5,423,816 and US 2010/0076495 A1.

SUMMARY OF THE INVENTION

The object of the present invention is to provide an improved implantable flexibly elastic or tensile device or plate and improved methods of use thereof for fixation of orthopedic structures or skeletal parts whereby the skeletal parts to which the device is fastened are biased toward one another and further expansion thereof is resisted. The device can be used for temporary or permanent fixation of the skeletal parts. The device can be pre-tensioned so as to provide a closure force between the skeletal parts or can be installed without pre-tension for thereby only resisting further expansion of the skeletal parts.

In one form thereof the present invention is directed to an implantable tensile device for fixation to skeletal parts. The device includes a body made of a biocompatible material having opposing fixation ends and a generally planar tensile portion therebetween. The tensile portion has opposing side edges and a longitudinal axis extending between the opposing fixation ends and generally centrally between the side edges. A fastener element at each of the fixation ends is adapted to engage a fastener whereby the fixation ends can be fastened to a skeletal part. A flexure slot extends into the tensile portion from a mouth on one of the sides to a terminal bottom located between the longitudinal axis and the opposing side. The tensile portion is made of a shape memory material whereby, upon separation of the fixation ends, the mouth of the flexure slot opens and the tensile portion elastically expands along the longitudinal axis whereby expansion of the skeletal parts to which the fixation ends are fastened is resisted and/or, by fastening the fixation ends to the skeletal parts while the tensile portion has been elastically expanded, the skeletal parts can be biased toward one another.

Preferably, one or more flexure slots are provided extending from a mouth at one of the sides into the tensile portion to a terminal bottom located between the longitudinal axis and the opposite side thereof; and, one or more flexure slots are provided extending from a mouth at the other one of the sides into the tensile portion to a terminal bottom located between the longitudinal axis and the opposite side thereof. More preferably, an even number of flexure slots are provided extending into the tensile portion from one of the sides and an odd number of flexure slots are provided extending into the tensile portion from the other one of the sides. The terminal bottom of each flexure slot preferably includes a round opening whereby each of the flexure slots and respective round opening are substantially keyhole shaped.

An abutment element can preferably be provided at one or both of the fixation ends. The abutment element is adapted to be engaged by an extension tool whereby the fixation ends can be separated and the tensile portion elastically expanded. The abutment element preferably comprises an aperture extending through a fixation end.

In another embodiment, a pair of fastener elements are provided at each of the fixation ends, each fastener element of each pair being located on opposing sides of the longitudinal axis. An abutment element is located between the pair of fastener elements at one or both of the fixation ends. The abutment element is adapted to be engaged by an extension tool whereby the fixation ends can be separated and the tensile portion elastically expanded. The abutment element preferably comprises an aperture extending through a fixation end.

In another embodiment, the device includes an alignment arm secured to and extending from one of the fixation ends. A sleeve means is secured to the other one of the fixation ends and is adapted to slidingly receive the alignment arm, whereby the skeletal parts are prevented from pivotal motion relative to one another and are allowed to expand and/or can be biased toward one another substantially linearly. A stop means can be provided on the alignment arm for limiting the sliding travel of the alignment arm through the sleeve means.

In yet another embodiment, the device includes a second generally planar tensile portion between the opposing fixation ends. The second tensile portion has opposing side edges and a second longitudinal axis. The second longitudinal axis extends between the opposing fixation ends and is generally centrally located between the sides of the second tensile portion. A second fastener element is provided at each of the fixation ends adapted to engage a fastener whereby the fixation ends can be fastened to a skeletal part. A flexure slot extends into the second tensile portion from a mouth on one of its sides to a terminal bottom located between the second longitudinal axis and its opposing side. The second tensile portion is made of a shape memory material whereby, upon separation of the fixation ends, the mouth of the flexure slots of both tensile portions may open and the tensile portions may elastically expand along their longitudinal axes whereby expansion of the skeletal parts to which the fixation ends are fastened is resisted and/or, by fastening the fixation ends to the skeletal parts while one or both of the tensile portions have been elastically expanded, the skeletal parts can be biased toward one another linearly and/or angularly. Preferably, the first tensile portion includes one or more flexure slots extending therein from one of its sides and includes one or more flexure slots extending therein from the other one of its sides, and the second tensile portion includes one or more flexure slots extending therein from one of its sides and includes one or more flexure slots extending therein from the other one of its sides. The first or second tensile portion can be effectively thinner than the other one of the first or second tensile portions, whereby the thinner tensile portion provides less resistance and a smaller biasing force than the thicker tensile portion. In this embodiment, a pair of abutment elements are preferably provided at each of the fixation ends. Preferably, the fastener elements comprise a hole extending through a fixation end adapted to receive a fastener in the form of a threaded screw having a head larger than the hole.

In another form thereof, the present invention is directed to a method of fixation of skeletal parts using an implantable tensile device that comprises: a body made of a biocompatible material; the body having opposing fixation ends and a generally planar tensile portion therebetween; wherein the tensile portion is made of a shape memory material whereby, upon separation of the fixation ends, the tensile portion elastically expands; a fastener element at each of the fixation ends adapted to engage a fastener whereby the fixation ends can be fastened to a skeletal part; and, an abutment element at each of the fixation ends, the abutment elements adapted to be engaged by an extension tool whereby the fixation ends can be separated and the tensile portion elastically expanded. The method of fixation includes the steps of: engaging the abutment elements at both of the fixation ends with an extension tool and separating the fixation ends and elastically expanding the tensile portion; fastening one fixation end to a skeletal part with a skeletal fastener by engaging its fastener element; fastening the other fixation end to a skeletal part with a skeletal fastener by engaging its fastener element; and, disengaging the extension tool from the abutment elements and releasing the fixation ends whereby the skeletal parts to which the fixation ends are fastened are biased toward one another and further expansion thereof is resisted. Preferably, the fastener element comprises a hole extending through a fixation end adapted to receive a skeletal fastener in the form of a threaded screw having a head larger than the hole and, during the steps of fastening, the threaded screw is inserted through the hole and threadingly engages the skeletal part. The abutment elements preferably comprise an aperture and the extension tool comprises pins adapted to engage the apertures, and the tool pins are received in the apertures during the steps of engaging and separating.

In yet another form thereof, the present invention is directed to a method of fixation of skeletal parts using an implantable tensile device that comprises: a body made of a biocompatible material; the body having opposing fixation ends and a generally planar tensile portion therebetween; wherein the tensile portion is made of a shape memory material whereby, upon separation of the fixation ends, the tensile portion elastically expands; a fastener element at each of the fixation ends adapted to engage a fastener whereby the fixation ends can be fastened to a skeletal part; and, an abutment element at one or both of the fixation ends, the abutment element adapted to be engaged by an extension tool whereby the fixation ends can be separated and the tensile portion elastically expanded. The method of fixation includes the steps of: fastening one fixation end to a skeletal part with a skeletal fastener by engaging its fastener element; engaging the abutment element of the unfastened fixation end with an extension tool and separating the fixation ends and elastically expanding the tensile portion; fastening the other fixation end to a skeletal part with a skeletal fastener by engaging its fastener element; and, disengaging the extension tool from the abutment element and releasing the fixation end whereby the skeletal parts to which the fixation ends are fastened are biased toward one another and further expansion thereof is resisted. Preferably, the fastener element comprises a hole extending through a fixation end adapted to receive a skeletal fastener in the form of a threaded screw having a head larger than the hole and, during the steps of fastening, the threaded screw is inserted through the hole and threadingly engages the skeletal part. The abutment elements preferably comprise an aperture and the extension tool comprises pins adapted to engage the apertures, and the tool pins are received in the apertures during the steps of engaging and separating.

BRIEF DESCRIPTION OF THE DRAWINGS

The above mentioned and other features of this invention, and the manner of attaining them, will become more apparent and the invention itself will be better understood by reference to the following description of the embodiments of the invention taken in conjunction with the accompanying drawings, wherein:

FIG. 5 is a top plan view similar to FIG. 3 but depicting the S-shaped plate for forming the sleeve means;

FIG. 6 is a top plan view of a stop means on the alignment arm constructed in accordance with the principles of the present invention;

FIG. 7 is a top plan view of another stop means on the alignment arm constructed in accordance with the principles of the present invention;

FIG. 8 is a top plan view of another implantable tensile device constructed in accordance with the principles of the present invention;

FIG. 9 is a top plan view of the device shown in FIG. 8 in an expanded configuration;

Figure 1:
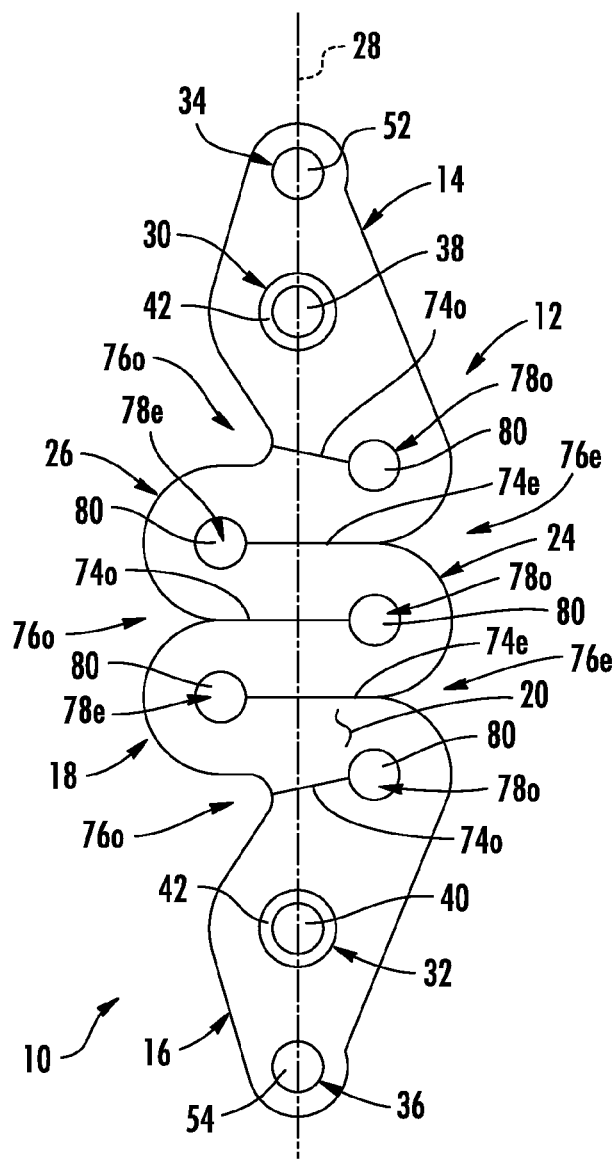
FIG. 1 is a top plan view of an implantable tensile device constructed in accordance with the principles of the present invention.

Corresponding reference characters indicate corresponding parts throughout the several views. Although the exemplification set out herein illustrates embodiments of the invention, in several forms, the disclosed embodiments are not intended to be exhaustive or to be construed as limiting the scope of the invention to the precise forms disclosed.

DETAILED DESCRIPTION OF THE PREFERRED EMBODIMENTS

Preferred embodiments of an implantable tensile device are shown in the drawings and designated by the numerals 10, 88, 90, 120 and 122. The devices includes a body 12 having opposing fixation ends 14, 16 and a tensile portion 18 therebetween. Body 12 is planar shaped and is made of a biocompatible material for surgically implanting and use within human and animal bodies for fixation of skeletal parts thereof. Additionally, body 12 and/or at least the tensile portion 18 thereof is made of a shape memory material whereby it can be elastically expanded. In this regard and more particularly, fixation as described and used herein includes attachment, alignment and/or containment of skeletal parts such as bones and tendons where such fixation requires some degree of flexibility. The devices hence have tensile characteristics such that, when fastened to skeletal parts, expansion thereof is resisted and/or the skeletal parts are biased toward one another.

The shape memory biocompatible material can be, for example, stainless steel, titanium, thermoplastic polymers, thermoset polymers, etc. Preferably, body 12 is made by cutting out of a larger planar sheet such as by laser cutting, wire electrical discharge machining (EDM), water jet, and/or molded to a desired planar thickness so as to form the desired shapes as shown. The embodiment of device 10 shown in FIGS. 1 and 1a and the other embodiments of the device will have a length, width and thickness as needed or desired relative to the skeletal parts and applicable forces for proper fixation thereof. For example, the embodiment of device 10 shown in FIGS. 1 and 1a can have a body 12 with a length of 0.50 to 2.0 inch and width of 0.50 to 1.0 inch, and a thickness of 0.030 to 0.150 inch as generally depicted in FIG. 1a.

Figure 1A:
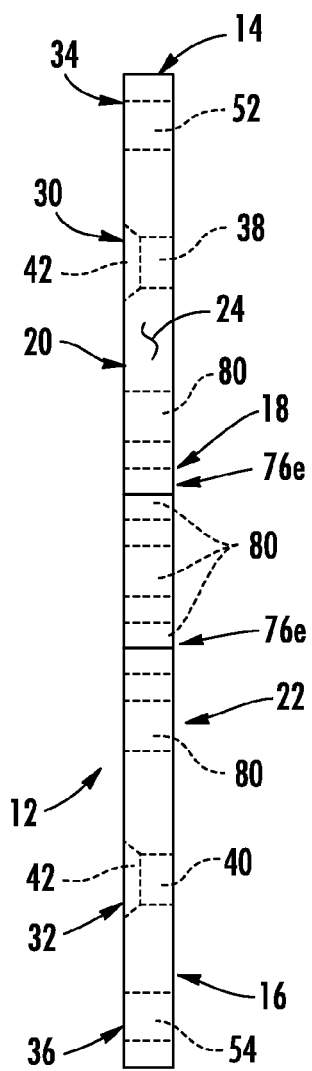
FIG. 1a is a side elevation view of the implantable tensile device shown in FIG. 1.

Referring now more particularly to the embodiment of the device 10 shown in FIGS. 1 and 1a, the body 12, and hence the fixation ends 14, 16 and the tensile portion 18, includes opposing face surfaces 20, 22 and opposing side edges 24, 26. A longitudinal axis 28 extends through the tensile portion 18 between the opposing fixation ends 14, 16 and is generally centrally located between the side edges 24, 26 as shown. Most preferably, longitudinal axis 28 extends through the fastener elements 30, 32 and the abutment elements 34, 36 which are located at respective fixation ends 14, 16. The tensile portion 18 is located between the fastener elements 30, 32. Also preferably, the fastener elements 30, 32 are located between the abutment elements 34, 36 or, stated differently, the abutment elements 34, 36 are distal of both the tensile portion 18 and the fastener elements 30, 32.

Figure 13:
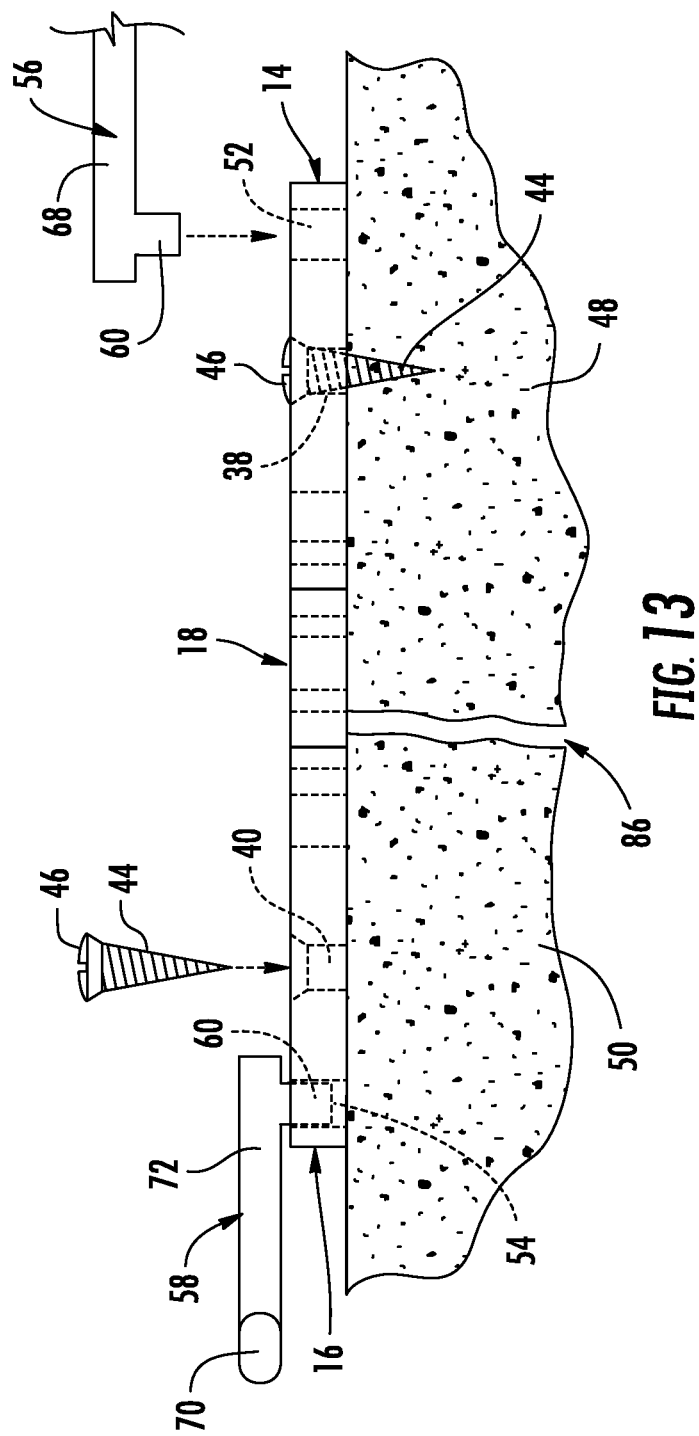
FIG. 13 is a cross sectional view of two skeletal parts with an implantable tensile device thereon and depicting the use of extension tools and threaded screw fasteners therewith.

The fastener elements 30, 32 are each preferably in the form of a respective fastener hole 38, 40 provided at and extending through each of the fixation ends 14, 16. The fastener holes 38, 40 include a chamfered edge 42 along the face surface 20. As shown in FIG. 13, fastener holes 38, 40 are adapted to engage a fastener or, more particularly, receive a threaded screw 44 therethrough whereby the fixation ends 14, 16 can be fastened to the skeletal parts 48, 50. Screws 44 are adapted to be threadingly driven into the skeletal parts 48, 50 in a known and customary manner and include a head 46 which is larger than the holes 38, 40 adapted to engage the chamfered edge 40.

The abutment elements 34, 36 are adapted to be engaged by an extension tool whereby the fixation ends 14, 16 can be separated and the tensile portion 18 elastically expanded. Preferably, the abutment elements 34, 36 are each in the form of a respective aperture 52, 54 provided at and extending through each of the fixation ends 14, 16. Apertures 52, 54 are adapted to be engaged by an extension tool such as the extension tool 56 shown in FIGS. 11-14 and the extension tool 58 shown in FIG. 15. The extension tools 56, 58 are provided with pins 60 adapted to be received in and engage the apertures 52, 54 and are thereby used to elastically expand the tensile portion 18 as more fully described hereinbelow.

Figure 12:
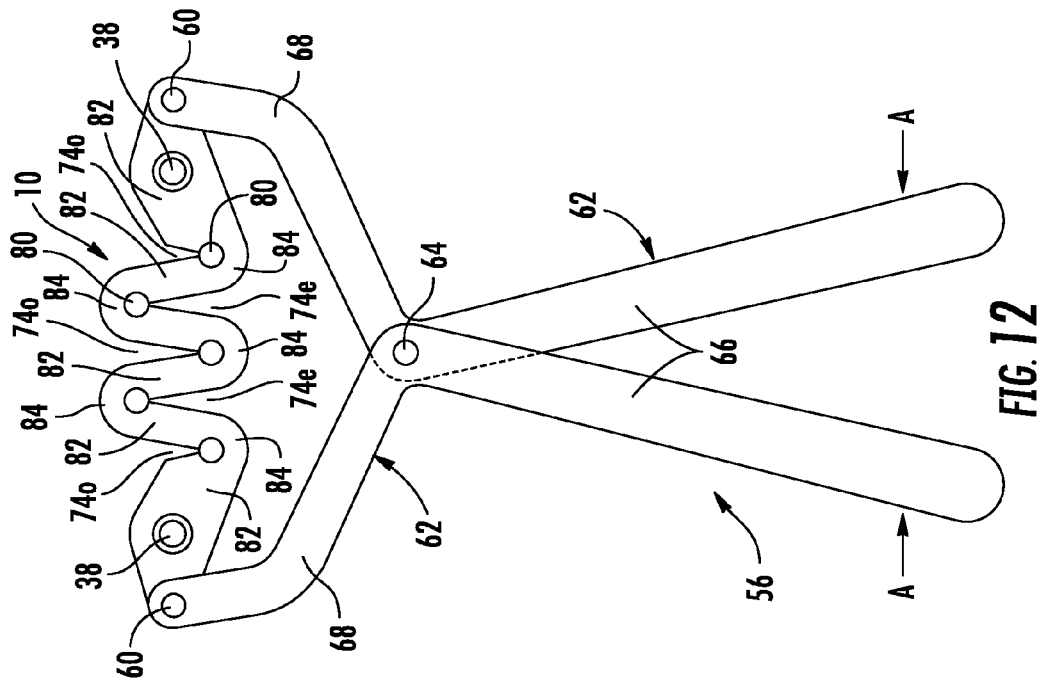
FIG. 12 is a view similar to FIG. 11 but showing the device in an expanded configuration.
Figure 11:
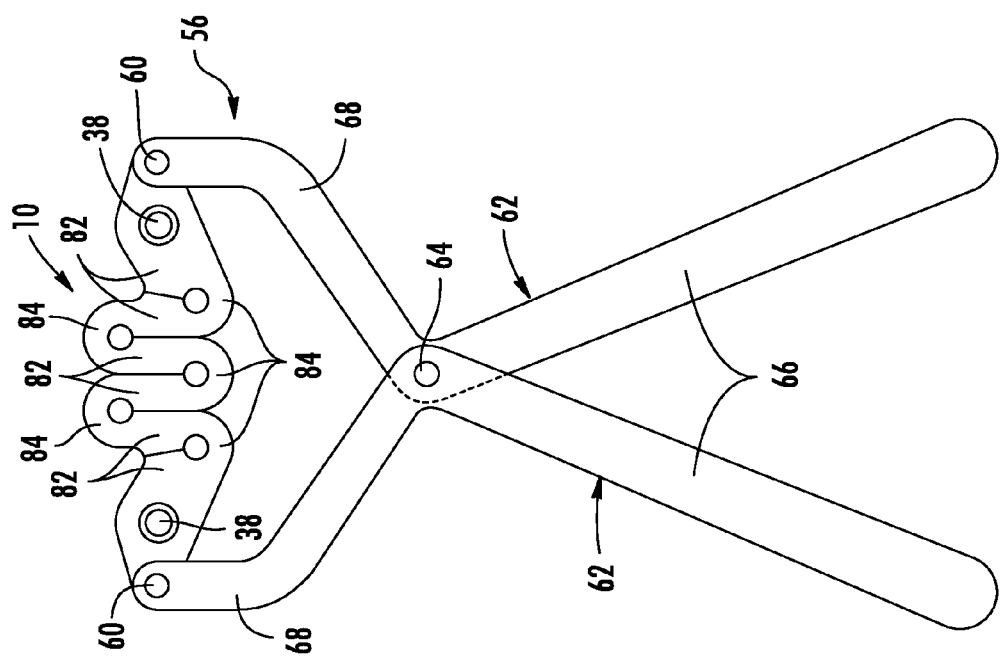
FIG. 11 is a diagrammatic top plan view of an extension tool engaged to the fixations ends of a tensile device prior to expansion of the device.

The extension tool 56 comprises a pair of arms 62 pivotally secured to one another with a pivot pin 64. Arms 62 include a handle portion 66 and a jaw portion 68. Tool pins 60 are provided at the terminal ends of jaw portions 68. Accordingly, as best seen in FIGS. 11, 12 and the right half of FIG. 13, the tool pins 60 of jaw portions 68 can be inserted into and in engagement with the apertures 52, 54 at each of the fixation ends 14, 16. By then grasping and compressing the handle portions 66 towards one another as depicted by the arrows A in FIG. 12, the fixation ends can be separated from one another and the tensile portion 18 can be elastically expanded as depicted between FIGS. 11 and 12.

Figure 15A:
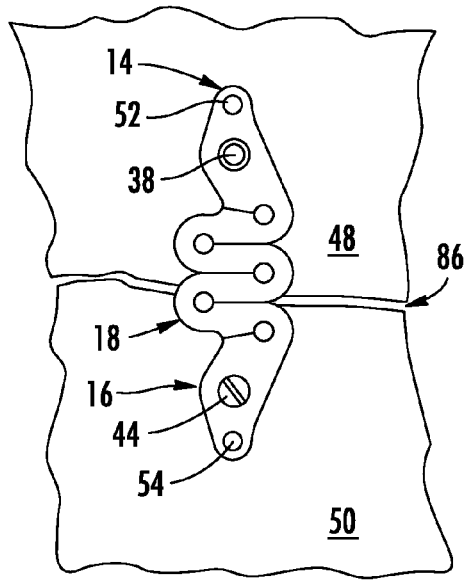
Figure 15B:
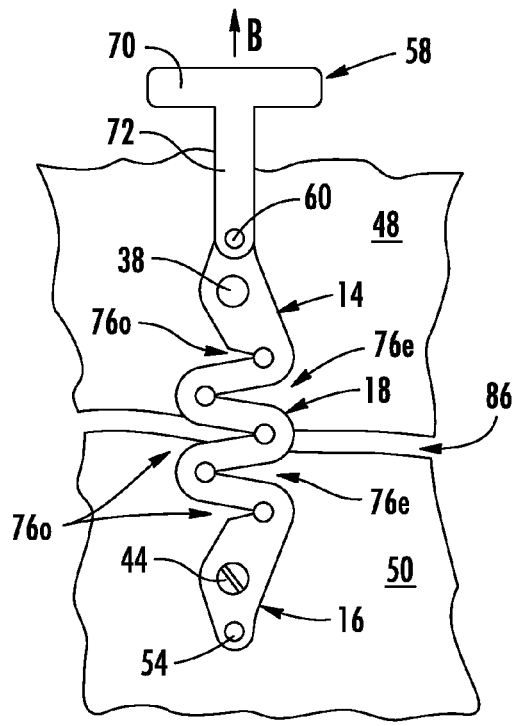
Figure 15C:
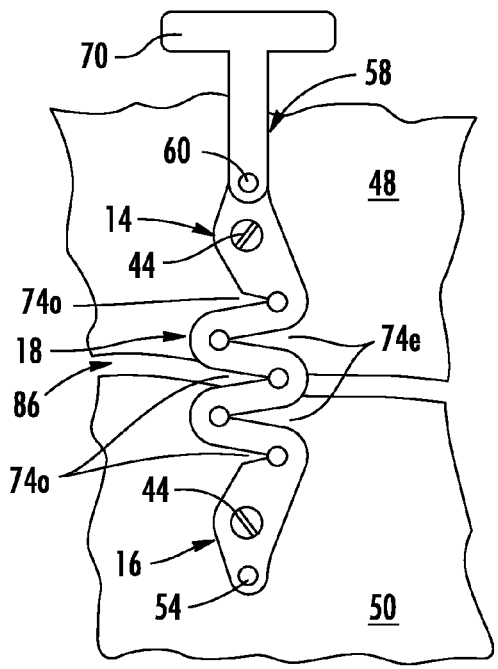

The extension tool 58 is T-shaped comprising a handle portion 70 and a draw portion 72. A tool pin 60 is provided at the terminal end of the draw portion 72. As best seen in FIGS. 15a-15c and the left half of FIG. 13, after one fixation end 14 or 16 is fastened to a skeletal part, the tool pin 60 of draw portion 72 can be inserted into and in engagement with the aperture 52 or 54 at the other fixation end 14 or 16. By then grasping and pulling the handle portion 70 as depicted by arrow B in FIG. 15b, the unfastened fixation end can be separated from the fastened fixation end and the tensile portion 18 can be elastically expanded.

Referring now again more particularly to FIGS. 1 and 1a, as previously mentioned, the tensile portion 18 is made of shape memory material and is adapted to elastically expand. In this regard, an even number of flexure slots 74e are cut into the tensile portion 18 extending from a rounded mouth 76e on the side edge 24 to a terminal bottom 78e which is located between the longitudinal axis 28 and the other side edge 26. Similarly, an odd number of flexure slots 74o are cut into the tensile portion 18 extending from a rounded mouth 76o on the side edge 26 to a terminal bottom 78o which is located between the longitudinal axis 28 and the other side edge 24. Preferably, a plurality of flexure slots 74e and a plurality of flexure slots 74o are provided, and each of the even flexure slots 74e are intermediate an odd flexure slot 74o. The terminal bottoms 78e, 78o of each flexure slot 74e, 74o include a round opening 80. Hence, each of the flexure slots 74e, 74o and their respective round opening 80 form a substantially keyhole shape as seen in FIG. 1.

The flexure slots 74e, 74o and round openings 80 also thereby form a plurality of U-shaped sections comprising beam members 82 extending from curved portions 84. See FIGS. 11 and 12. The relative locations of the flexure slots 74e, 74o and the location and size of the round openings 80 are such that the cross-sectional thickness of the beam members 82 is greater than the cross-sectional thickness of the curved portions 84. Accordingly, in view of their relative cross-sectional thicknesses and shape, when the fixation ends 14, 16 are separated, the curved portions 84, and to a lesser degree the beam members 82, will flex and the tensile portion will elastically expand from the position shown in FIG. 11 to the position shown in FIG. 12 whereat the flexure slots 74 and mouths 76e, 76o thereof are opened. Because the tensile portion 18 is made of shape memory material, upon release of the fixation ends 14, 16, the curved portions 84 and beam members 82 will return to their original shape and the tensile portion 18 will contract back to its original shape as shown in FIG. 11.

Figure 14A:
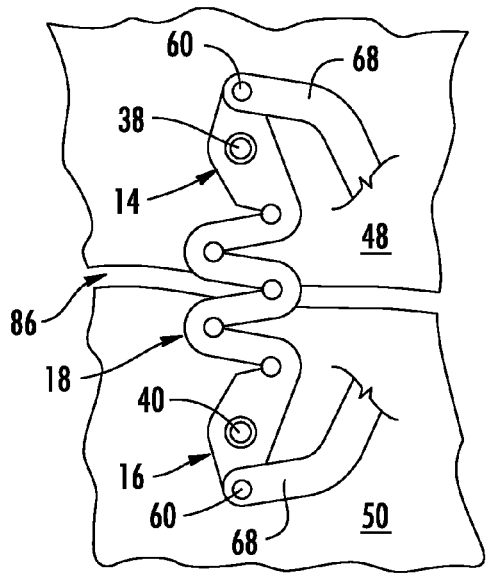
FIGS. 14a-14d are top elevation views of a tensile device and extension tool depicting a method of use thereof for fixation of skeletal parts in accordance with the principles of the present invention; and, FIGS. 15a-15d are top elevation views of a tensile device and another extension tool depicting another method of use thereof for fixation of skeletal parts in accordance with the principles of the present invention.
Figure 14B:
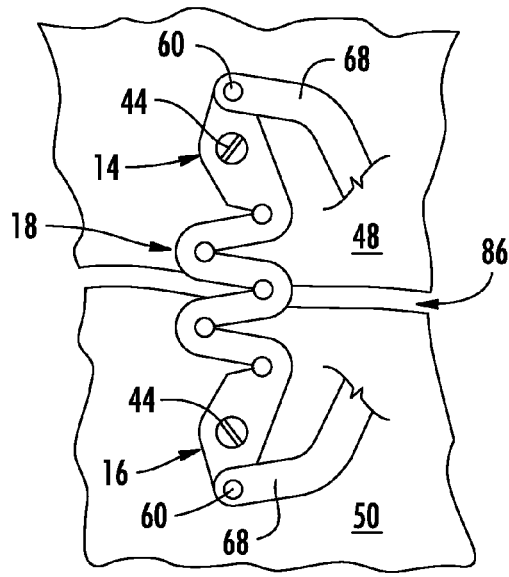
Figure 14C:
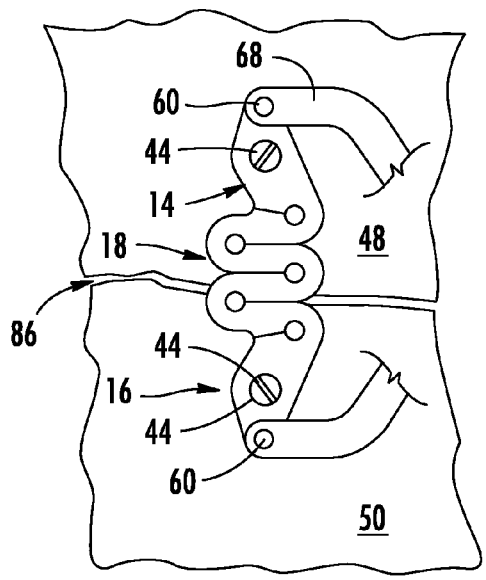
Figure 14D:
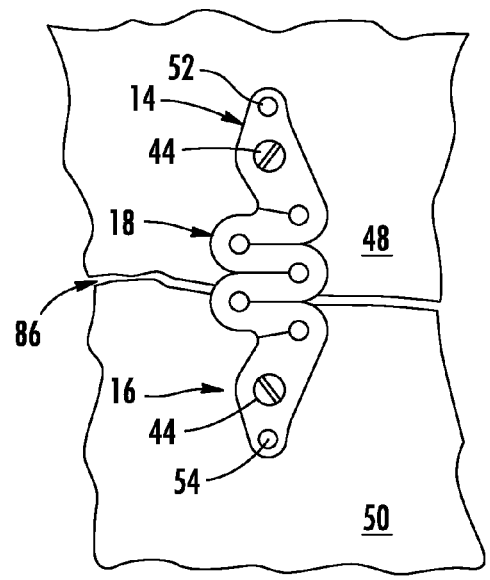

As depicted in FIGS. 14a-14d, the device 10 is used by surgically implanting for fixation of skeletal parts 48, 50 which, for example, have been fractured. Oftentimes, after such a fracture, the skeletal parts do not fit tightly together and will have a gap 86 therebetween as diagrammatically shown. Here, an extension tool 56 can be used for initially engaging the abutment elements 34, 36 at the fixation ends 14, 16 by inserting the pins 60 of each jaw portion 68 into a respective abutment element aperture 52, 54. By grasping and compressing the handle portions 66 towards one another (as depicted by the arrows A in FIG. 12), the fixation ends are separated from one another and the tensile portion 18 is elastically expanded as shown in FIG. 14a. While the tensile portion 18 is expanded, a fastener screw 44 is inserted through the fastener hole 38 and driven into and fastened to the skeletal part 48, and a fastener screw 44 is inserted through the fastener hole 40 and driven into and fastened to the skeletal part 50. Accordingly, as shown in FIG. 14b, the fixation end 14 is fastened to the skeletal part 48 and the fixation end 16 is fastened to the skeletal part 50. Thereafter, the handle portions 66 are released thereby also releasing the fixation ends 14, 16 as depicted in FIG. 14c, and the extension tool 56 is disengaged therefrom by removing the pins 60 from their respective aperture 52, 54 as depicted in FIG. 14d. Accordingly, the skeletal parts 48, 50 are now biased toward one another thereby bringing them closer together and closing the gap 86, and further expansion thereof is resisted.

Figure 15D:
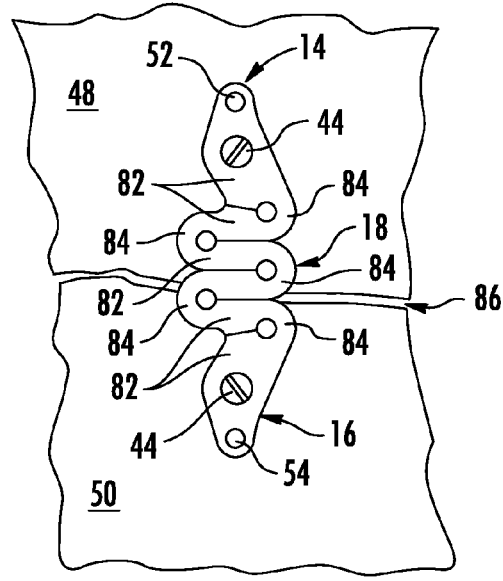

In another preferred method of using the device 10, a tool 58 can be used as depicted in FIGS. 15a-15d. Here, as shown in FIG. 15a, the fixation end 16 is first fastened to skeletal part 50 by inserting a fastener screw 44 through the fastener hole 40 and threadingly driving it and fastening it into the skeletal part 50. As depicted in FIG. 15b, the abutment element 34 at the unfastened fixation end 14 is then engaged by inserting the pin 60 of extension tool 58 into the abutment element aperture 52 and, by grasping and pulling the handle portion 70 as depicted by arrow B, the unfastened fixation end 14 is separated from the fastened fixation end 16 and the tensile portion 18 is elastically expanded. While the tensile portion 18 is expanded, a fastener screw 44 is then inserted through the fastener hole 38 and driven into and fastened to the skeletal part 48, thereby fastening the other fixation end 14 to the skeletal part 48. See FIG. 15c. The extension tool 58 is thereafter disengaged by removing its pin 60 from aperture 52 as depicted in FIG. 15d and thereby also releasing the now also fastened fixation end 14. Accordingly, the skeletal parts 48, 50 are now biased toward one another thereby bringing them closer together and closing the gap 86, and further expansion thereof is resisted.

It is noted that in the methods of use described herein above, the device 10 is essentially pre-tensioned using an extension tool 56, 58 and, thereafter, fastened between the skeletal parts 48, 50. If needed or desired, the pre-tension force can be measured such as by employing a tension scale or other known means (not shown) on the extension tools 56, 58. Alternatively, the tension force per unit displacement/expansion length can be pre-measured and, during installation/ fixation to the skeletal parts, the surgeon can separate the fixation ends 14, 16 a desired distance which corresponds to a desired pre-tension force.

It is also noted that device 10 can be fastened to the skeletal parts 48, 50 as described above, but without first expanding the tensile portion 18 and, in such use, the device will not be pre-tensioned such that, after fixation, the skeletal parts will not be biased toward one another. However, in such use, the device 10 will allow flexibility and will resist further expansion of the skeletal parts 48, 50. In connection with device 10, it is also noted that, because a single fastener screw 44 is used at each fixation end 14, 16, the fastened skeletal parts can rotate about the longitudinal axis of the fastener screw relative to the fixation end to which they are fastened.

Figure 2A:
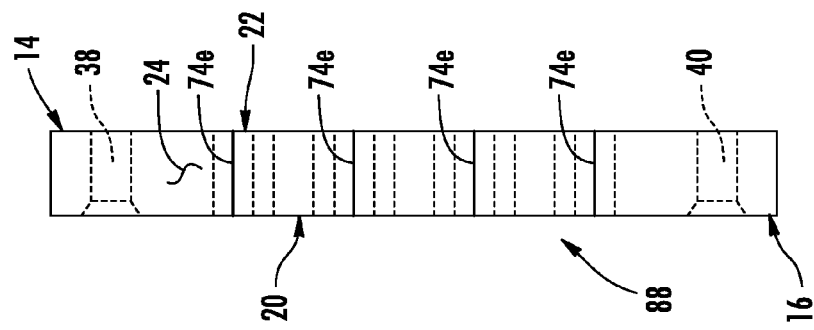
FIG. 2a is a side elevation view of the implantable tensile device shown in FIG. 2.
Figure 2:
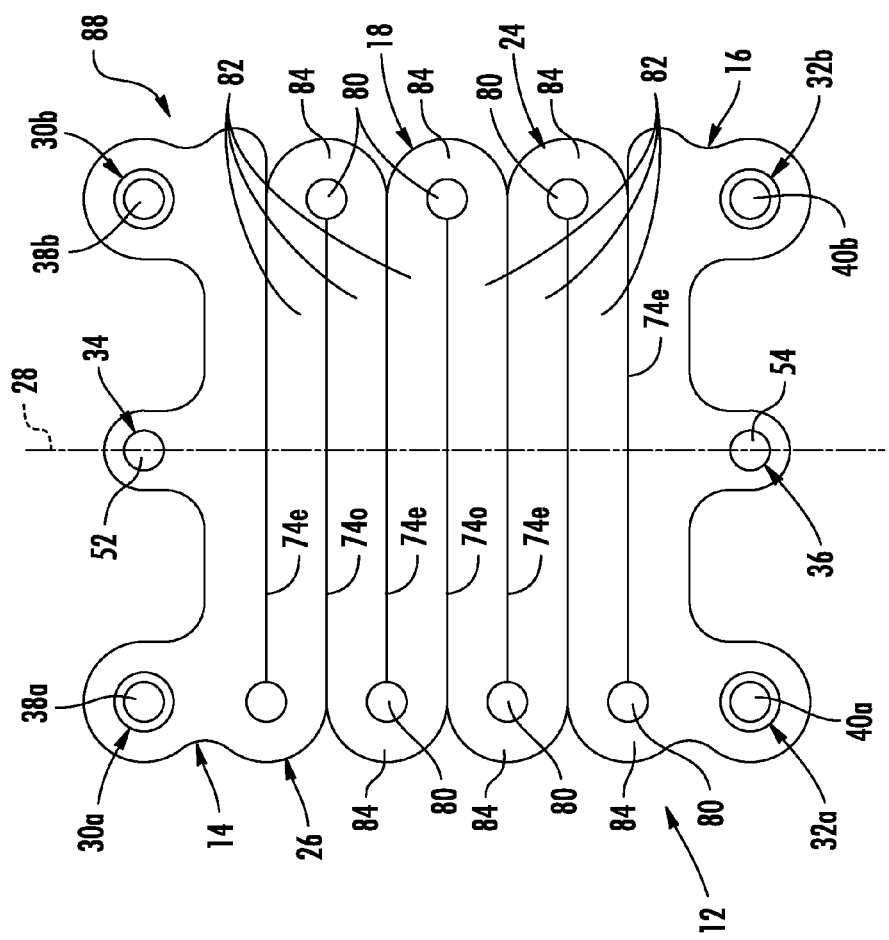
FIG. 2 is a top plan view of another implantable tensile device constructed in accordance with the principles of the present invention.
Figure 3:
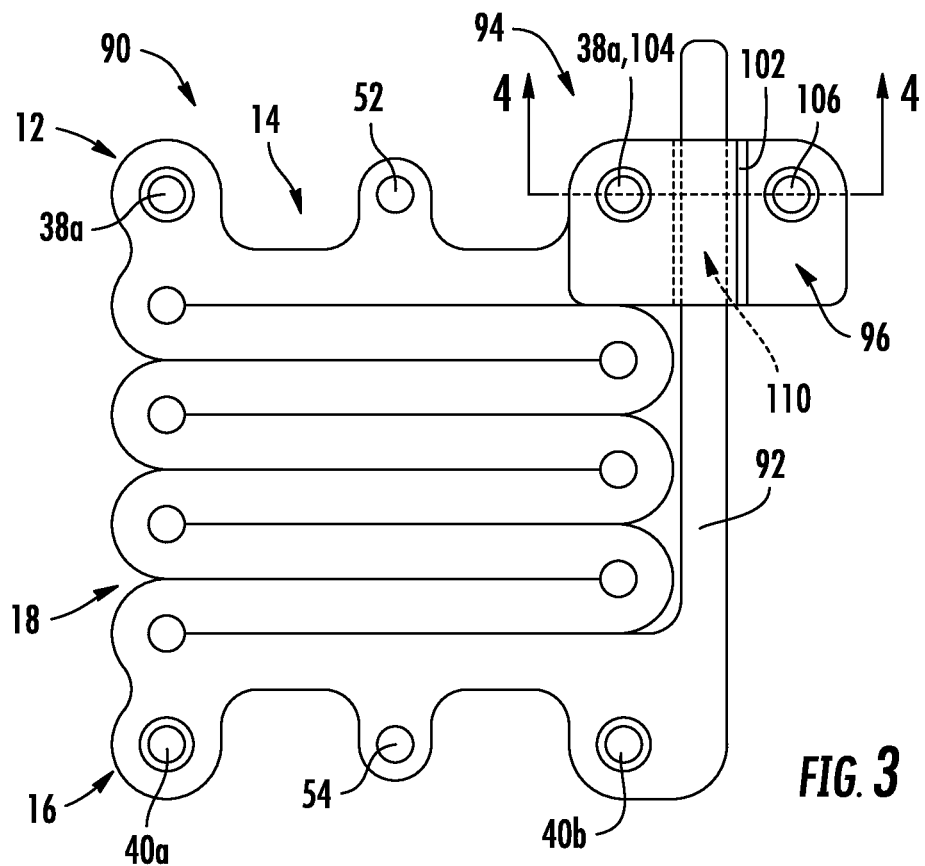
FIG. 3 is a top plan view of an implantable tensile device similar to that of FIG. 2 and including an alignment arm sleeve means.

Another preferred embodiment is shown in FIGS. 2 and 2a and is designated by the numeral 88. Device 88 is substantially similar to device 10 in that it includes a body 12; fixation ends, 14, 16; a planar tensile portion 18 therebetween; a longitudinal axis 28 extending through the tensile portion 18 between the opposing fixation ends 14, 16 and generally centrally located between the side edges 24, 26; etc. Device 88, however, is provided with a pair of fastener elements 30a and 30b at its fixation end 14, and a pair of fastener elements 32a and 32b at its fixation end 16. Each of the fastener elements 30a and 32a are located on opposing sides of the longitudinal axis 28 from fastener elements 30b and 32b. The abutment element 34 at fixation end 14 is located between the fastener elements 30a and 30b and, preferably, is centered with the longitudinal axis 28. Similarly, the abutment element 36 at fixation end 16 is located between the fastener elements 32a and 32b and, preferably, is also centered with the longitudinal axis 28.

Device 88 is used for fixation of skeletal parts and is expanded using extension tools 56, 58 substantially similar to device 10 as described above, except that a pair of fastener screws 44 are used at each fixation end 14, 16, one at each of the fastener holes 38a, 38b, 40a and 40b. Accordingly, unlike device 10, the skeletal parts will not rotate relative to the fixation end 14, 16 to which they are fastened.

Another preferred embodiment is shown in FIGS. 3-7 and is designated by the numeral 90. Device 90 is substantially similar to device 88 except that an alignment arm 92 is secured to and extends from the fixation end 16 preferably, for example, by cutting out of the same sheet material forming the body 12 thereof. Alignment arm 92 extends parallel to the body 12 and generally along the side edge 24 from the fixation end 16 up to a past the fixation end 14. A sleeve means 94 is secured to the fixation end 14 and is adapted to slidingly receive the alignment arm 92 such that the fixation ends 14, 16 and the skeletal parts to which they are fastened are prevented from pivotal motion relative to one another while the fixation ends 14, 16 are, nevertheless, allowed to expand and/or be biased toward one another substantially linearly along the alignment arm 92.

Figure 4:
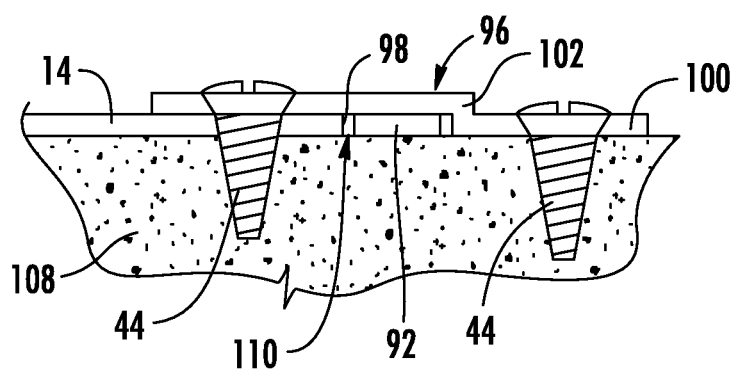
FIG. 4 is a cross sectional view of the sleeve means and alignment arm taken along line 4-4 of FIG. 3.

Sleeve means 94 includes an S-shaped plate 96 having an upper sheet section 98 and a lower sheet section 100 joined along a bend 102. Upper sheet section 98 includes a fastener hole 104 adapted to align with the fastener hole 38b of the fixation end 14 and receive a fastener screw 44 therethrough. Lower sheet section 100 includes a fastener hole 106 adapted to receive a fastener screw 44 therethrough. After the device 90 is positioned on a skeletal part 108 as best seen in FIG. 4, plate 96 is positioned placing its upper sheet section 98 over the fixation end 14 and with fastener hole 38b aligned with fastener hole 104. A fastener 44 is received through both the fastener holes 104 and 38b and is driven into the skeletal part 108, and a fastener 44 is received through the fastener hole 106 and is also driven into the skeletal part 108. Accordingly, with both the fixation end 14 and the S-shaped plate 96 now secured to the skeletal part, an elongate sleeve 110 is formed and is bound by the skeletal part 108, bend 102, upper sheet section 98 and the fixation end 14. The alignment arm 92 extends through the elongate sleeve 110 and may slide therethrough thereby preventing the skeletal parts to which the fixation ends 14, 16 are fastened from pivotal motion relative to one another and allowing them to expand and/or can be biased toward one another substantially linearly.

As can be seen in FIGS. 6 and 7, stop means 112 can be provided on the alignment arm 92 and preferably at its terminal end for limiting the sliding travel of the arm 92 through the sleeve means 94. In the embodiment of FIG. 6, the stop means 112 includes a plurality of holes 114 along the arm 92 and a fastener 116 adapted to be received through and secured in any one of the holes 114. The fastener 116 is larger than the elongate sleeve 110 and thereby prevents the arm 92 from being withdrawn therethrough. Therefore, the amount of sliding travel of arm 92 is adjustable by selection of the hole 114 whereat the fastener 116 is secured.

The stop means 112 of FIG. 7 is provided by forming the terminal end of the alignment arm 92 into a T-shape. In this regard, the arm is formed with a cross bar 118 generally perpendicular to the arm 92, thereby forming the T-shape. The cross bar 118 is larger than the elongate sleeve 110 thereby preventing the arm 92 from being withdrawn therethrough.

Figure 10:
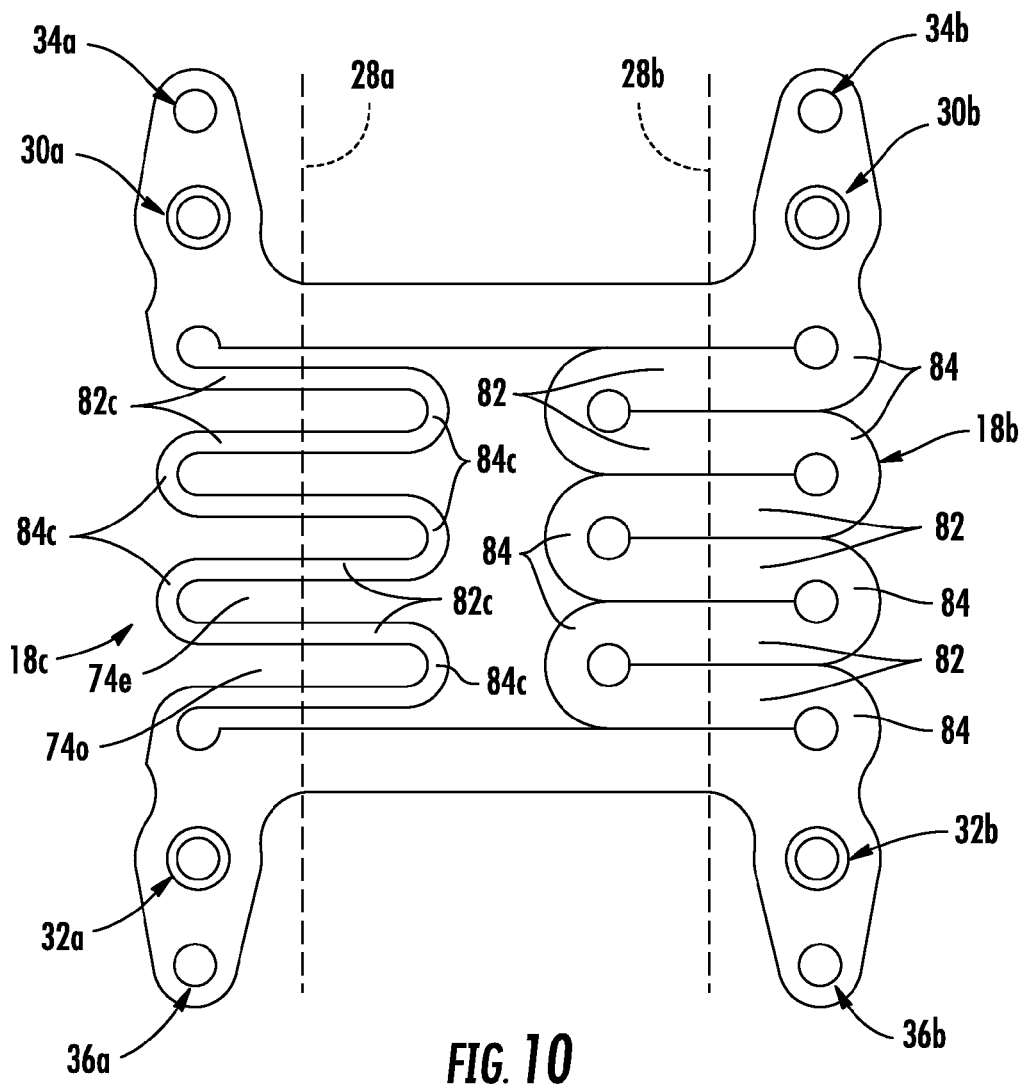
FIG. 10 is a top plan view of another implantable tensile device constructed in accordance with the principles of the present invention.

Another preferred embodiment is shown in FIGS. 8-10 and is designated by the numeral 120. Device 120 is substantially similar to the devices 10 and 88 in that it includes a body 12 and fixation ends, 14, 16. However, device 120 includes two side by side tensile portions 18a, 18b between the fixation ends 14, 16. The device 120 and both tensile portions 18a, 18b are similarly cut out of the same sheet material. Tensile portions 18a, 18b are substantially similar to tensile portion 18 of device 10 and each includes a respective longitudinal axis 28a, 28b.

Device 120 is provided with a pair of fastener elements 30a and 30b at its fixation end 14, and a pair of fastener elements 32a and 32b at its fixation end 16. Each of the fastener elements 30a and 32a are located on opposing sides of both of the longitudinal axes 28a, 28b from fastener elements 30b and 32b. That is, both of the longitudinal axes 28a, 28b are located between the fastener elements 30a, 32a and 30b, 32b. Device 120 is also provided with a pair of abutment elements 34a, 34b at its fixation end 14, and a pair of abutment elements 36a, 36b at its fixation end 16. The abutment elements 34a, 36a are longitudinally aligned with and are located distal of both fastener elements 30a, 32a. Similarly, the abutment elements 34b, 36b are longitudinally aligned with and are located distal of both fastener elements 30b, 32b.

When using device 120, as depicted in FIG. 9, one of the tensile portions 18a can be elastically expanded further than the other tensile portion 18b such that the resulting biasing force between fastening elements 30a and 32a is greater than the resulting biasing force between fastening elements 30b and 32b. Hence, the skeletal parts to which the fixation ends 14, 16 are fastened are similarly biased toward one another and along an arc path.

Referring now to the FIG. 10, the device 122 as shown is similar to device 120, except that the tensile portion 18c includes beam portions 82c and curved portions 84c having cross sections which are smaller than the cross sections of the beam portions 82 and curved portions 84 of tensile portion 18b. It is noted that the shape of beam portions 82c and curved portions 84c are preferably the same as beam portions 82 and curved portions 84 (forming keyhole shapes as described herein above) but, in FIG. 10, the tensile portion 18c is shown diagrammatically for illustration purposes depicting it smaller/thinner relative to tensile portion 18b without the keyhole shapes.

As should be appreciated, the tensile portion 18c provides less resistance and a smaller biasing force to the skeletal parts to which the fastener elements 30a, 32a are fastened than the resistance and biasing force which the tensile portion 18b provides to the skeletal parts to which the fastener elements 30b, 32b are fastened. That is, a differential resistance and biasing force is provided between the fastener elements 30a, 32a than between the fastener elements 32a, 32b.

While this invention has been described as having an exemplary design, the present invention may be further modified within the spirit and scope of this disclosure. This application is therefore intended to cover any variations, uses, or adaptations of the invention using its general principles.

What is claimed is:

1. A tensile device for fixation to skeletal parts, said device comprising:
   a body made of a biocompatible material;
   said body having opposing fixation ends and a generally planar tensile portion therebetween, said tensile portion having opposing side edges and a longitudinal axis, said longitudinal axis extending between said opposing fixation ends and being generally centrally located between said side edges;
   a fastener element at each of said fixation ends adapted to engage a fastener whereby said fixation ends can be fastened to a skeletal part;
   a flexure slot extending into said tensile portion from a mouth on one of said side edges to a terminal bottom located between said longitudinal axis and the opposing side edge;
   wherein said tensile portion is made of a shape memory material whereby, upon separation of said fixation ends, said mouth of said flexure slot opens and said tensile portion elastically expands along said longitudinal axis whereby expansion of the skeletal parts to which said fixation ends are fastened is resisted and/or, by fastening said fixation ends to the skeletal parts while said tensile portion has been elastically expanded, the skeletal parts can be biased toward one another;
   wherein one or more flexure slots are provided extending from a mouth at one of said side edges into said tensile portion to a terminal bottom located between said longitudinal axis and the opposite side edge thereof;
   one or more flexure slots are provided extending from a mouth at the other one of said side edges into said tensile portion to a terminal bottom located between said longitudinal axis and the opposite side edge thereof; and,
   a tool abutment element at one or both of said fixation ends, said abutment element adapted to be engaged by an extension tool whereby said fixation ends can be separated and said tensile portion elastically expanded.

2. The tensile device of claim 1 wherein an even number of flexure slots are provided extending into said tensile portion from one of said sides and an odd number of flexure slots are provided extending into said tensile portion from the other one of said sides.

3. The tensile device of claim 2 wherein said abutment element comprises an aperture extending through a fixation end.

4. The tensile device of claim 3 wherein said terminal bottom of each flexure slot includes a round opening whereby each of said flexure slots and respective round opening are substantially keyhole shaped.

5. The tensile device of claim 2 wherein said terminal bottom of each flexure slot includes a round opening whereby each of said flexure slots and respective round opening are substantially keyhole shaped.

6. The tensile device of claim 1 wherein said fastener element comprises a hole extending through a fixation end adapted to receive a fastener in the form of a threaded screw having a head larger than said hole.

7. The tensile device of claim 1 wherein said abutment element comprises an aperture extending through a fixation end.

8. The tensile device of claim 1 wherein said terminal bottom of said flexure slot includes a round opening whereby said flexure slot and respective round opening is substantially keyhole shaped.

9. A tensile device for fixation to skeletal parts, said device comprising:
- a body made of a biocompatible material;
- said body having opposing fixation ends and a generally planar tensile portion therebetween, said tensile portion having opposing side edges and a longitudinal axis, said longitudinal axis extending between said opposing fixation ends and being generally centrally located between said side edges;
- a fastener element at each of said fixation ends adapted to engage a fastener whereby said fixation ends can be fastened to a skeletal part;
- a flexure slot extending into said tensile portion from a mouth on one of said side edges to a terminal bottom located between said longitudinal axis and said opposing side edge;
- wherein said tensile portion is made of a shape memory material whereby, upon separation of said fixation ends, said mouth of said flexure slot opens and said tensile portion elastically expands along said longitudinal axis whereby expansion of the skeletal parts to which said fixation ends are fastened is resisted and/or, by fastening said fixation ends to the skeletal parts while said tensile portion has been elastically expanded, the skeletal parts can be biased toward one another;
- wherein an even number of flexure slots are provided extending into said tensile portion from one of said side edges and an odd number of flexure slots are provided extending into said tensile portion from the other one of said side edges;
- wherein said fastener element comprises a hole extending through a fixation end adapted to receive a fastener in the form of a threaded screw having a head larger than said hole; and,
- wherein said terminal bottom of said flexure slot includes a round opening whereby said flexure slot and respective round opening is substantially keyhole shaped.

10. The tensile device of claim 9 further comprising an abutment element at one or both of said fixation ends, said abutment element adapted to be engaged by an extension tool whereby said fixation ends can be separated and said tensile portion elastically expanded.

11. The tensile device of claim 10 wherein said abutment element comprises an aperture extending through a fixation end.

12. The tensile device of claim 9 wherein said fastener element comprises a hole extending through a fixation end adapted to receive a fastener in the form of a threaded screw having a head larger than said hole.

* * * * *